United States Patent
Jasinschi et al.

(10) Patent No.: US 9,747,902 B2
(45) Date of Patent: Aug. 29, 2017

(54) METHOD AND SYSTEM FOR ASSISTING PATIENTS

(75) Inventors: Radu Serban Jasinschi, Nuenen (NL); Murtaza Bulut, Eindhoven (NL); Luca Bellodi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 158 days.

(21) Appl. No.: 14/116,419

(22) PCT Filed: Jun. 1, 2012

(86) PCT No.: PCT/IB2012/052769
§ 371 (c)(1),
(2), (4) Date: Oct. 23, 2014

(87) PCT Pub. No.: WO2012/164534
PCT Pub. Date: Dec. 6, 2012

(65) Prior Publication Data
US 2015/0081299 A1    Mar. 19, 2015

(30) Foreign Application Priority Data
Jun. 1, 2011    (EP) .................................... 11168527

(51) Int. Cl.
G10L 17/00    (2013.01)
G10L 17/22    (2013.01)
A61B 5/16    (2006.01)
A61B 5/00    (2006.01)
G10L 25/63    (2013.01)
(Continued)

(52) U.S. Cl.
CPC .............. G10L 17/22 (2013.01); A61B 5/165 (2013.01); A61B 5/4088 (2013.01); G10L 25/63 (2013.01); G10L 25/66 (2013.01); G10L 15/26 (2013.01)

(58) Field of Classification Search
CPC ....... G06K 9/00302; G10L 17/26; A61B 5/00; A61B 5/168
USPC .................................................. 704/207, 270
See application file for complete search history.

(56) References Cited

U.S. PATENT DOCUMENTS 5,950,026 A     9/1999  Jessop
6,011,991 A *   1/2000  Mardirossian ....... A61B 5/0476
                                                   600/544
(Continued)

FOREIGN PATENT DOCUMENTS

CN      101783998 A      7/2010
CN      101897633 A     12/2010
(Continued)

OTHER PUBLICATIONS

Satyanarayanan M et al. "The Case for VM-Based Cloudlets in Mobile Computing", IEEE PERvasive Computing, IEEE Service Center, CA, vol. 8, No. 4, Oct. 1, 2009, pp. 14-23.
(Continued)

Primary Examiner — Daniel Abebe

(57) ABSTRACT

A system for use in assisting a user in a social interaction with another person is provided, the system being configured to determine whether the user recognizes the person and, if it is determined that the user does not recognize the person, to provide information to the user about the person. A corresponding method and computer program product for performing the method are also provided.

13 Claims, 5 Drawing Sheets

(51) Int. Cl.
*G10L 25/66* (2013.01)
*G10L 15/26* (2006.01)

(56) References Cited

U.S. PATENT DOCUMENTS

| | | | |
|---|---|---|---|
| 6,309,361 B1* | 10/2001 | Thornton | A61B 5/0484 600/544 |
| 7,155,456 B2* | 12/2006 | Abbott, III | G06F 17/30017 |
| 7,305,618 B2 | 12/2007 | Jasinschi | |
| 7,627,475 B2* | 12/2009 | Petrushin | G10L 17/26 704/231 |
| 8,965,770 B2* | 2/2015 | Petrushin | G10L 17/26 704/270 |
| 9,223,837 B2* | 12/2015 | Djugash | G06F 17/30554 |
| 2003/0182123 A1* | 9/2003 | Mitsuyoshi | G10L 17/26 704/270 |
| 2007/0222772 A1 | 9/2007 | Amick | |
| 2007/0238934 A1* | 10/2007 | Viswanathan | A61B 5/16 600/300 |
| 2008/0256445 A1 | 10/2008 | Olch et al. | |
| 2008/0256446 A1 | 10/2008 | Yamamoto | |
| 2009/0002178 A1* | 1/2009 | Guday | A61B 5/0002 340/573.1 |
| 2009/0083205 A1 | 3/2009 | Dishongh et al. | |
| 2010/0145134 A1 | 6/2010 | Madsen | |
| 2010/0196861 A1 | 8/2010 | Lunner | |
| 2010/0278318 A1* | 11/2010 | Flockhart | G10L 17/26 379/88.04 |
| 2010/0325078 A1* | 12/2010 | Lee | G06F 19/345 706/47 |
| 2010/0325218 A1* | 12/2010 | Castro | G06Q 50/01 709/206 |
| 2011/0096939 A1 | 4/2011 | Ichimura | |
| 2015/0032535 A1* | 1/2015 | Li | G06Q 30/0255 705/14.53 |
| 2015/0262016 A1* | 9/2015 | Rothblatt | A61B 5/0476 348/77 |

FOREIGN PATENT DOCUMENTS

| | | |
|---|---|---|
| CN | 102056036 A | 5/2011 |
| CN | 104375650 A | 2/2015 |
| JP | 2003533768 A | 11/2003 |
| JP | 2004246767 A | 9/2004 |
| JP | 2004275220 A | 10/2004 |
| WO | 0186464 A1 | 11/2001 |
| WO | 2010033461 A2 | 3/2010 |
| WO | 2011011413 A2 | 1/2011 |

OTHER PUBLICATIONS

Marques, O. et al. "Wireless multimedia technologies for assisted living". Second LACCEI International Latin American and Caribbean Conference for Engineering and Technology, 2004. "Challenges and Opportunities for Engineering Education, Research and Development". Jun. 2-4, 2004, Miami, Florida USA.
Narayanan. N.. "Ameliorating cognitive Impairments: Research Challenges in Designing Mobile, Multimodal and Adaptive Interfaces for Context-Aware Assistance". Paper presented at CHI'01 Workshop on Distributed and Disappearing User Interfaces in Ubiquitous Computing, Technical Report 2001-6, Germany, pp. 11-18.
Baille, L. et al. "A Supportive Multimodal Mobile Robot for the Home". Lecture Notes in Computer Science, 2004, vol. 3196/2004, 375-383.
Ekman, P. et al. Facial action coding system. Consulting Psychologist Press, 1977.
Ekman, P. et al. "Universal and cultural differences in the judgments of facial expressions of emotions". Journal of Personality and Social Psychology, 53:712-717, 1987.

Feldman, L.. "Valence focus and arousal focus: Individual differences in the structure of affective experience". Journal of Personality and Social Psychology, 69:153-166, 1995.
Wang, H. et al. , "A Prototype of a computer-aided system for Alzheimer's disease patients". Philips Research Technical Note PR-TN 2009/00715, 2009.
Mann, Steve (2013): Wearable Computing. In: Soegaard, Mads and Dam, Rikke Friis (eds.). "The Encyclopedia of Human-Computer Interaction, 2nd Ed.". Aarhus, Denmark: The Interaction Design Foundation. Available online at http://www.interaction-design org/encyclopedia/wearable_computing html.
Bulut, M. "Emotional speech resynthesis", PhD thesis, University of Southern California, 2007.
Donnelly, M. et al. "A Mobile Multimedia Technology to Aid Those with Alzheimer's Disease", Multimedia IEEE, vol. 17, Issue 2, pp. 42-51, Apr.-Jun. 2010.
Kautz, H. et al. "An overview of the assisted cognition project", AAAI-2002 Workshop on Automation as Caregiver: The Role of Intelligent Technology in Elder Seattle, WA (2002).
Helal, S. et al. "Smart Phone Based Cognitive Assistant", 2nd Int'l Workshop on Ubiquitous Computing for Pervasive Healthcare Applications, Springer, 2003.
Giraldo, C. et al. "mPCA—A Mobile Patient Care-Giving Assistant for Alzheimer Patients", First International Workshop on Ubiquitous Computing for Cognitive Aids (UbiCog'02). In conjunction with The Fourth International Conference on Ubiquitous Computing, UbiComp 2002. Sunday Sep. 29, 2002 in Goteborg, Sweden.
Astell a. "REAFF—A framework for developing technology to address the needs of people with dementia", Proceedings of the First International Workshop on Reminiscence Systems (RSW-2009) , pp. 5-10, Cambridge, UK, Sep. 5, 2009.
Alm, N. "Making software accessible to people with severe memory deficits", Proceedings of Accessible Design in the Digital World, Dundee Scotland, Aug. 15-19, 2005.
Alm, N. et al. "A cognitive prosthesis an communication support for people with dementia ", Neuropsychological Rehabilitation, vol. 14(112), pp. 117-134, 2004.
Gowans, G. et al. "Designing CIRCA. A multimedia conversation aid for reminiscence intervention in dementia care environments", Proceedings of the 5th European Academy of Design Conference, Barcelona, Apr. 28-30, 2003.
Alm et al: "A Cognitive Prosthesis and Communication Support for People With Dementia"; Neuropsychological Rehabilitation, 2004, vol. 14, pp. 117-134.
Mann: Wearable Computing: a First Step Toward Personal Imaging; Computer, vol. 30, No. 2, pp. 25-32, Feb. 1997.
"Alzheimer's Behavior Management:Managing Common Symptoms and Problems"; Dec. 2007, 5 Page Document, Downloaded From http://helpguide.org/elder/alzheimers_behavior_problems. htm, on Dec. 12, 2009.
"Devices Aid in Tracking Lost Alzheimer's Patients"; Associated Press Article, Aug. 2007, Downloaded From http://www.msnbc. msn.com/id/20237586, Aug. 2007.
Butcher:"A Camera to Help Dementia Patients"; MIT Technology Review, Dec. 10, 2007, Downloaded From http://www.technologyreview.com/new/409170/a-camera-to-help-dementia-patients/ in Dec. 12, 2009.
Kautz et al: "Foundations of Assisted Cognition Systems"; Technical Report CSE-02-AC-01, Department of Computer Science and Engineering, University of Washington, 2003, 25 Page Article.
Wang et al: "A Prototype of a Computer-Aided System for Alzheimer's Disease Patients"; Technical Note PR-TN 2009/00715, Jul. 2009, 22 Page Document.
Bulut: "Emotional Speech Resynthesis"; PhD Thesis, University of Southern California, May 2008, 269 Page Document.
Patient Compliance Net: "Medical Devices to Help Improve Patient Compliance and Medication Adherence"; downloaded from http/www.patientcompliance.net, Aug. 2009.
Philips Lifeline, Advertisement, https://web.archive.org/web/20091212033315/http://www.lifelinesys.com/, 2009.

(56) References Cited

OTHER PUBLICATIONS

Lincoln: "TAT Augmented ID"; Jul. 14, 2009, Retrieved From the Internet: http://ww.talse/blog/tat-augmented-id/, Jul. 17, 2012.

* cited by examiner

METHOD AND SYSTEM FOR ASSISTING PATIENTS

CROSS-REFERENCE TO PRIOR APPLICATIONS

This application is the U.S. National Phase application under 35 U.S.C. §371 of International Application Serial No. PCT/IB2012/052769 filed on Jun. 1, 2012, which claims the benefit of application Ser. No. 11/168,527.7, filed on Jun. 1, 2011. These applications are hereby incorporated by reference herein.

TECHNICAL FIELD OF THE INVENTION

The invention relates to a method and system for assisting people having memory impairment, such as that caused by Alzheimer's disease, in social interactions.

BACKGROUND TO THE INVENTION

People with early and mid-stage Alzheimer's disease (AD) who display mental impairments, such as memory loss, reduced executive function and attention, can generally still perform their daily tasks reasonably well, usually with help from a family member, friend or care provider.

However, people with AD (or memory and cognitive impairment in general) can find social interactions, such as a conversation with another person (who may be a caregiver, doctor, friend) to be difficult, since they usually do not remember who the person is or the relevant information about them and may not be able to fully follow the conversation. The loss of memory in these interactions results in stress for the person with AD, and this is usually reflected in undesired behavior of the person, thus making it difficult for them to maintain a healthy social life.

Although systems exist for helping elderly people perform their basic tasks and activities, these systems are not specifically designed with people who have significant memory impairment, such as Alzheimer's disease, in mind, and are therefore not particularly suited to this use.

There is therefore a need for a method and system for assisting a person having memory impairment in social interactions.

SUMMARY OF THE INVENTION

Various aspects of the invention are set out in the following statements.
1. A system for use in assisting a user in a social interaction with another person, the system being configured to determine whether the user recognizes the person and, if it is determined that the user does not recognize the person, to provide information to the user about the person.
2. A system as defined in statement 1, wherein the system is configured to determine whether the user recognizes the person by determining an emotional state of the user.
3. A system as defined in statement 2, wherein the system comprises one or more sensors for measuring physiological characteristics of the user, and wherein the system is configured to determine an emotional state of the user based on the measured physiological characteristics.
4. A system as defined in statement 2 or 3, wherein the system is configured to determine an emotional state of the user by analyzing the speech of the user during the interaction.
5. A system as defined in any of statements 1 to 4, wherein the system is configured to determine whether the user recognizes the person by playing an audio and/or video message and monitoring the response of the user to the message.
6. A system as defined in any of statements 1 to 4, wherein the system is configured to determine whether the user recognizes the person by using a speech recognition algorithm to analyze the speech by the user and/or the person during the interaction.
7. A system as defined in any of statements 1 to 6, wherein the system comprises:
image capturing means for capturing an image or a series of images of the person;
a processor for applying a facial recognition algorithm to the captured image to identify the person, and for obtaining information on the identified person; and
a user interface for presenting the information obtained on the identified person to the user if it is determined that the user does not recognize the person.
8. A system as defined in any of statements 1 to 7, wherein the system comprises:
a microphone for recording the speech of the person during the interaction;
a processor for processing the recorded speech using a voice recognition algorithm to identify the person, and for obtaining information on the identified person; and
a user interface for presenting the information obtained on the identified person to the user if it is determined that the user does not recognize the person.
9. A system as defined in any preceding statement, wherein the system is further configured to provide information to the person if it is determined that the user does not recognize the person, the information indicating to the person that the user does not recognize them.
10. A system as defined in any preceding statement, the system comprising a microphone for recording speech during the interaction between the user and the person, and wherein the system is further configured to, on determining that the interaction is complete, generate a summary of the interaction for the user and provide the summary to a user interface for presentation to the user.
11. As system as defined in statement 10, wherein the system is further configured to determine an emotional state of the user during the interaction, and the system is configured to generate the summary of the interaction for the user based on the recorded speech and the determined emotional state.
12. A system as defined in any preceding statement, wherein the system is further configured to determine whether the user remembers or understands the purpose of the interaction with the person, and, if it is determined that the user does not remember or understand the purpose of the interaction, the system is configured to provide information to the user about the purpose of the interaction.
13. A system as defined in any preceding statement, wherein the system is further configured to monitor the interaction to determine whether the user is following and understanding the interaction as the interaction progresses, and, if it is determined that the user is not following or understanding the interaction, the system is configured to provide information to the user about the interaction.
14. A system as defined in statement 13, wherein the system is configured to determine the context of the interaction, such that the system can provide context-specific information to the user about the interaction if it is determined that the user is not following or understanding the interaction.

15. A system as defined in statement 12, 13 or 14, wherein the system is configured to monitor (i) the speech of the user to determine if the user is able to commence and follow the interaction; (ii) the speech of the user to determine the emotional state of the user; (iii) the speech of both the user and the person to determine the context of the interaction and the current dialogue; and/or (iv) the physiological response of the user during the interaction to determine whether the user remembers or understands the purpose of the interaction with the person and/or to determine whether the user is following and understanding the interaction as the interaction progresses.

16. A method for use in assisting a user in a social interaction with another person, the method comprising:
determining whether the user recognizes the person; and
if it is determined that the user does not recognize the person, providing information to the user about the person.

17. A method as defined in statement 16, wherein the step of determining whether the user recognizes the person comprises determining an emotional state of the user.

18. A method as defined in statement 17, wherein the method further comprises the step of measuring physiological characteristics of the user; and wherein the step of determining the emotional state of the user uses the measured physiological characteristics.

19. A method as defined in statement 17 or 18, wherein the step of determining an emotional state of the user further comprises analyzing the speech of the user during the interaction.

20. A method as defined in any of statements 16 to 19, wherein the step of determining whether the user recognizes the person comprises playing an audio and/or video message and monitoring the response of the user to the message.

21. A method as defined in any of statements 16 to 19, wherein the step of determining whether the user recognizes the person comprises analyzing the speech by the user and/or the person during the interaction.

22. A method as defined in any of statements 16 to 21, wherein the method further comprises the steps of:
capturing an image or a series of images of the person;
applying a facial recognition algorithm to the captured image to identify the person;
obtaining information on the identified person; and
presenting the information obtained on the identified person to the user if it is determined that the user does not recognize the person.

23. A method as defined in any of statements 16 to 22, wherein the method further comprises:
recording the speech of the person during the interaction;
processing the recorded speech using a voice recognition algorithm to identify the person;
obtaining information on the identified person; and
presenting the information obtained on the identified person to the user if it is determined that the user does not recognize the person.

24. A method as defined in any of statements 16 to 23, wherein the method further comprises the step of providing information to the person if it is determined that the user does not recognize the person, the information indicating to the person that the user does not recognize them.

25. A method as defined in any of statements 16 to 24, the method further comprising the steps of:
recording speech during the interaction between the user and the person;
on determining that the interaction is complete, generating a summary of the interaction for the user; and
providing the summary to a user interface for presentation to the user.

26. A method as defined in statement 25, wherein the method further comprises the steps of
determining an emotional state of the user during the interaction, and
generating the summary of the interaction for the user based on the recorded speech and the determined emotional state.

27. A method as defined in any of statements 16 to 26, wherein the method further comprises the steps of:
determining whether the user remembers or understands the purpose of the interaction with the person; and
if it is determined that the user does not remember or understand the purpose of the interaction, providing information to the user about the purpose of the interaction.

28. A method as defined in any of statements 16 to 27, wherein the method further comprises the steps of
monitoring the interaction to determine whether the user is following and understanding the interaction as the interaction progresses; and
if it is determined that the user is not following or understanding the interaction, providing information to the user about the interaction.

29. A method as defined in statement 28, wherein the method comprises determining the context of the interaction, such that context-specific information can be provided to the user about the interaction if it is determined that the user is not following or understanding the interaction.

30. A method as defined in statement 27, 28 or 29, wherein the method further comprising:
monitoring (i) the speech of the user to determine if the user is able to commence and follow the interaction; (ii) the speech of the user to determine the emotional state of the user; (iii) the speech of both the user and the person to determine the context of the interaction and the current dialogue; and/or (iv) the physiological response of the user during the interaction to determine whether the user remembers or understands the purpose of the interaction with the person and/or to determine whether the user is following and understanding the interaction as the interaction progresses.

31. A computer program product comprising computer-readable code, the code being configured such that, on execution by a suitable computer or processor, the computer or processor performs the method defined in any of statements 16 to 30.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Although the invention will be described below with reference to a system and method for a person having Alzheimer's disease (AD), it will be appreciated that the invention is suitable for use by any person having a memory impairment that affects their ability to interact socially.

Figure 1:
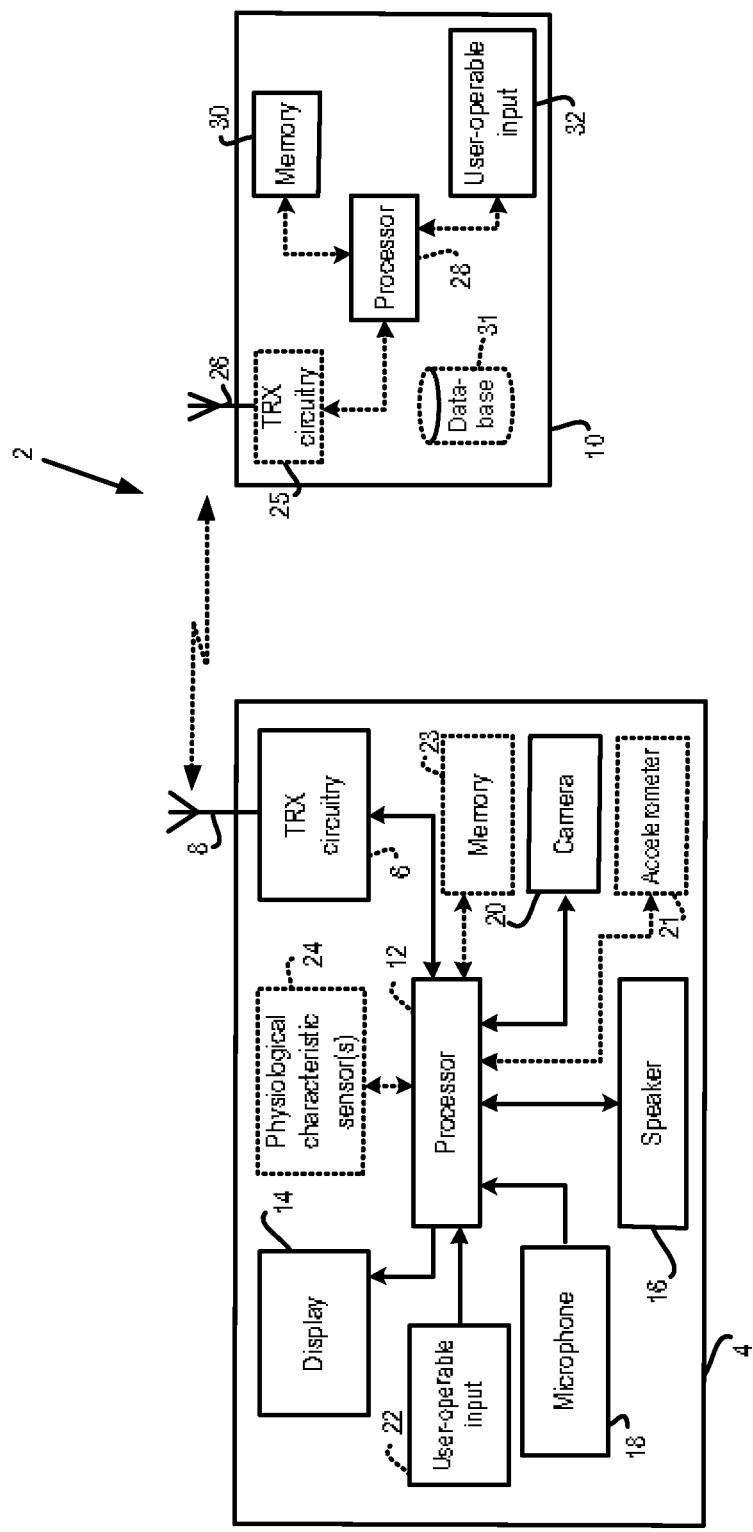
FIG. 1 is a block diagram of a system according to the invention.

An exemplary embodiment of the system 2 according to the invention is shown in FIG. 1. The system 2 comprises a portable or mobile device 4 that is worn or carried by the user of the system 2 (i.e. the person having the memory impairment). The mobile device 4 can take any suitable form, but in a preferred embodiment the mobile device 4 is a pendant that is worn around the user's neck, although in alternative embodiments the mobile device 4 can be a mobile telephone (such as a smartphone) or a PDA).

The mobile device 4 comprises transceiver circuitry 6 and associated antenna 8 for communicating with a base unit 10. The transceiver circuitry 10 can be configured to use any suitable communications protocol for communicating with the base unit 10, including, for example, Bluetooth or Wi-Fi, or a mobile communications protocol, such as GSM, etc.

The mobile device 4 also comprises visual display 14, speaker 16, microphone 18, camera 20, movement or orientation sensor 21 (such as an accelerometer and/or magnetometer) and user-operable input 22 that are each connected to a processor 12. These components form a user interface that allows the user to interact with the mobile device 4, and vice versa. The mobile device 4 can also include memory 23 for storing data collected by the microphone 18 and camera 20 prior to transmission by the transceiver circuitry 6. In some embodiments of the invention, the mobile device 4 also includes one or more sensors 24 for sensing physiological characteristics of the user (for example, heart rate, breathing rate and/or perspiration), although it will be appreciated that these sensors 24 can be provided externally or separate from the mobile device 4 (for example so that they can be attached directly to the skin of the user) and interface with the mobile device 4 to communicate the measurements to the processor 12.

When external to the mobile device 4, the sensors 24 can form a body area network (BAN) or personal area network (PAN). Data collected by the sensors 24 can be transmitted directly to the base unit 10 in order to be evaluated, or it can be sent first to the mobile device 4 in order to be processed if there is any time-critical requirement within the system.

It will be appreciated that the mobile device 4 can include further components to those illustrated in FIG. 1. For example, the device 4 can include an orientation sensor and a light sensor.

The display 14 is provided to show text or graphical messages and/or video clips to the user. The speaker 16 is provided to output audio (usually speech, although other audio content can be provided), which may be associated with visual information being provided by the display 14.

The microphone 18 is used to detect and record sound in the vicinity of the device 4, primarily speech by the user and a person or people with which the user is interacting.

The camera 20 is used to capture images, particularly images of a person or people with which the user is interacting with. The images can be still images or a sequence of video.

The user-operable input 22 allows the user to interact with the mobile device 4, and may comprise a single input, such as a button or key, multiple inputs, such as a keyboard, or other form of user-operable input, such as a touch screen associated with the display 14.

In the illustrated embodiment, the base unit 10 comprises transceiver circuitry 25 and associated antenna 26 for communicating with the mobile device 4. As in the mobile device 4, the transceiver circuitry 25 in the base unit 10 can be configured to use any suitable communications protocol, including, for example, Bluetooth or Wi-Fi, or a mobile telecommunications protocol, such as GSM, etc. In this embodiment, the base unit 10 is a computer or server located in the home of the user or a server at a remote location that communicates wirelessly with the mobile device 4.

In alternative embodiments, it will be appreciated that, where the base unit 10 is at a remote location, the mobile device 4 may communicate wirelessly with an intermediate device, such as a router and/or a home computer that communicates with the base unit 10 via the internet, and therefore the transceiver circuitry 25 and antenna 26 in the base unit 10 may be substituted by suitable components for connecting the base unit 10 to the internet.

The base unit 10 comprises a processor 28, memory 30, database 31 and user-operable input 32. The database 31 is used to store information about people that the user has or could interact with, past interactions, patient data for the user, different communication problems the user might have, the support that should be provided to the user when these problems occur, topics of conversation and other relevant information. The user-operable input 32 allows the user or a healthcare provider to interact with the base unit 10, and may comprise a keyboard, touch screen, etc.

As described above, people with AD (and other memory impairments) can find social interactions, such as a conversation with another person (who may be a caregiver, doctor, friend) to be difficult, since the person may not recognize the person they are speaking to, or they may forget the thread of the conversation. However, the system 2 according to embodiments of the invention provides information that assists the user (who has AD or another memory impairment) to recognize the person they are communicating with, reducing the initial confusion for the user and helping to prevent the user's lack of memory translating into stress.

During the interaction, the system 2 can monitor the user to determine if they have recognized the person they are communicating with and the context of the interaction and to determine the user's emotional response or whether the user is becoming stressed by the interaction and further support can be provided by the system 2 as required.

According to embodiments of the invention, the system 2 can identify the context and the topic of the conversation in order to provide context-relevant support to better assist the user during the interaction.

Embodiments of the invention can also provide feedback to the person that the user is interacting with, the feedback indicating whether the user recognizes them or needs assistance in or during the interaction, and this allows the person to adapt the way in which they are interacting with the user.

In addition, once the user has completed their interaction with the person, the system 2 can provide the user with information about the interaction to improve the user's recollection of the conversation.

The system 2 can process multimodal data, such as audio, video, text, lights and haptics to aid a person with AD or memory impairment to interact socially, while accounting for their memory impairment as well as their emotional state. Having such an assistance system 2 as described herein can help to improve the quality of life, particularly the social life, of people with AD.

Figure 2:
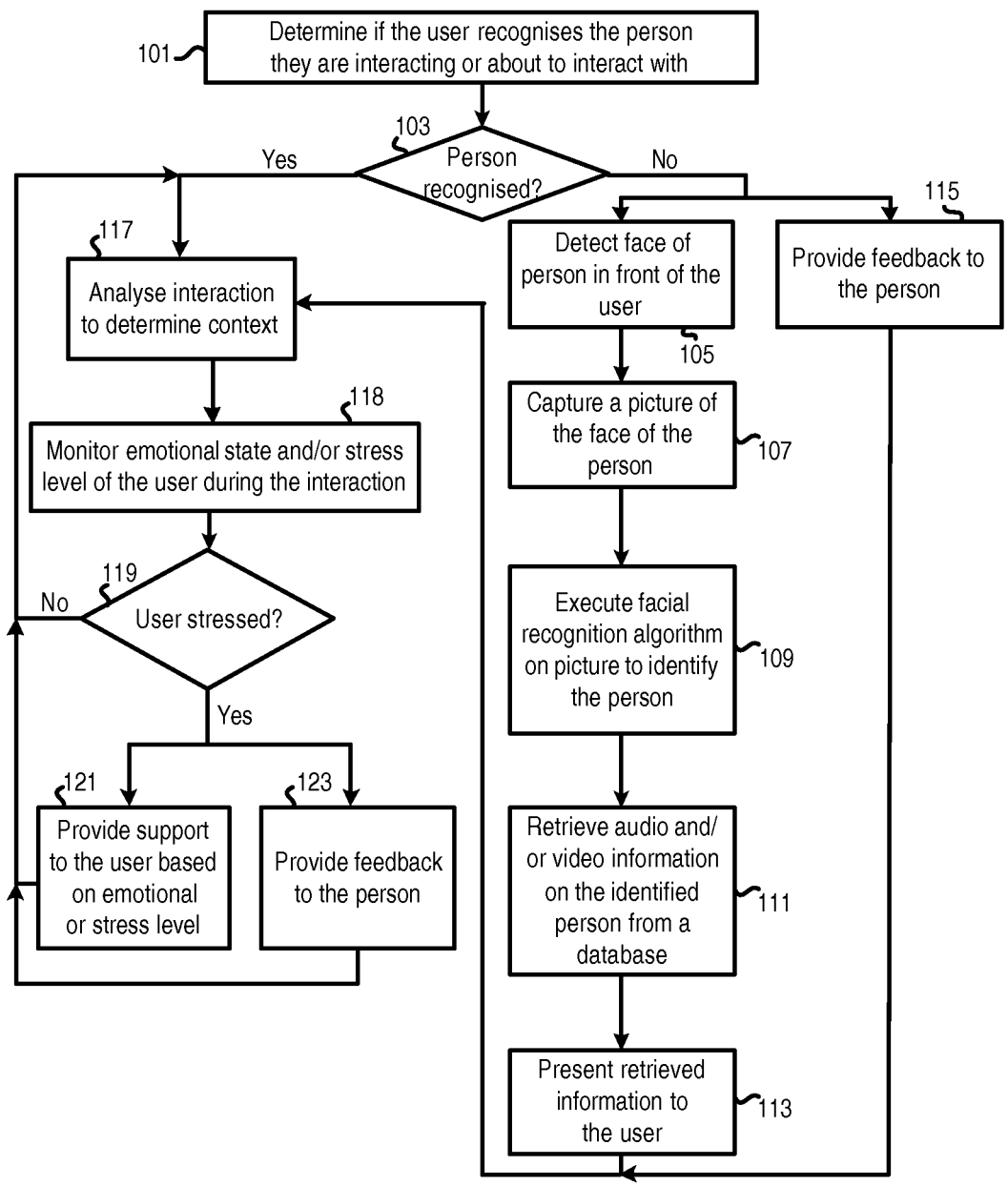
FIG. 2 is a flow chart illustrating a method according to a first embodiment.

A first embodiment will now be described with reference to the flow chart in FIG. 2. In the illustrated embodiment, if the user does not recognize the person with which they are interacting, the system 2 identifies the person using facial recognition technology and provides the user with information about that person in order to help the user recognize the person and the purpose of the interaction. The system 2 also monitors the emotional state/stress level of the user throughout the interaction, and provides additional support as required.

The method can be activated on detection of a person in front of the user (for example by analyzing images obtained by the camera 20 or light detected by another light sensor) or on detection of speech by the user (for example by analyzing the sound recorded by the microphone 18) or a predetermined time before an interaction is scheduled to take place (which may be recorded in an electronic calendar for the user stored in the mobile device 4).

The method starts with step 101 in which the system 2 determines if the user recognizes the person that they are about to interact with (or have started interacting with). This step can comprise the mobile device 4 broadcasting an audio message directly asking the user whether they recognize the person. In this case, the user can respond with a yes/no answer which can be identified by processing the output from the microphone 18 in the mobile device 4.

This step could also comprise recording the initial part of the conversation using the microphone 18 and analyzing the speech by the user and person using a speech recognition algorithm. The content of the conversation at this stage can indicate whether the user has recognized the person.

Alternatively, or in addition, this step can comprise monitoring the emotional state of the user for signs that the user has or has not recognized the person. For example, this step could involve measuring one or more physiological characteristics of the user, such as heart rate, heart rate variability, skin conductivity, breathing rate, perspiration, or any other characteristic that is an indicator of the stress level or emotional state of the user. The characteristics can be measured by, for example, the dedicated sensor(s) 24 in the mobile device 4. Alternatively, a breathing rate can be measured by processing the output of the microphone 18 to identify the sound associated with the breathing of the user, and the heart rate can be measured from video data of the user's skin.

The emotional state of the user could also be determined from measurements of the voice level or tone of the user obtained via the microphone 18.

Where an emotional state or stress level is to be determined, the characteristic measurements (or the raw data from the sensors 24, microphone 18 and/or camera 20) are transmitted to the base unit 10, and the processor 28 processes the measurements or data to determine the stress level or emotional state of the user. The result of the processing (i.e. an emotional or stress level) will have an associated probabilistic value, indicating how reliable the determination is. The result of the processing can then be used as an indicator of whether the user recognizes the person that they are interacting with.

Figure 3:
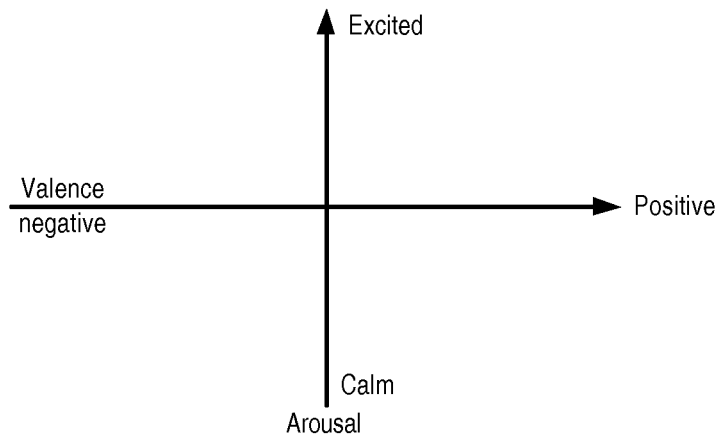
FIG. 3 is a diagram illustrating possible emotional states of a user.

The first part of the processing involves classifying and quantifying the measured physiological characteristics and mapping them to an emotional state. The mapping is preferably done according to a simple scheme, for example as shown in FIG. 3, in which the emotional state of the user is characterized by discrete values in two dimensions.

These two basic dimensions of emotional response can usefully characterize nearly any experience. Valence represents overall happiness encoded as positive (e.g. happy), neutral, or negative (e.g. sad, angry) and arousal represents the intensity level of emotion, encoded as excited, neutral, or calm. Many commonly named emotions (especially those corresponding to physical responses to the environment) can easily be positioned in the valence-arousal figure. Those skilled in the art will be aware of techniques for mapping measured physiological characteristics such as heart rate, heart rate variability, skin temperature, breathing rate, perspiration and galvanic skin response, to the valence-arousal Figure, and these techniques will not be described in detail herein.

Those skilled in the art will appreciate that the system 2 could process the sensor data in a different way to that described above in order to characterize a greater number of emotional states for the user. For example, a third dimension could be added to the diagram indicating the stress or tension of the user.

If the user has not recognized the person (determined in step 103), the method moves to steps 105-113 in which the system 2 identifies the person using facial recognition technology and provides the user with information about that person in order to help the user recognize the person and the purpose of the interaction.

In step 105, the face of a person interacting with the user is detected. This is preferably performed by the camera 20 in the mobile device 4, which continuously or periodically (e.g. every 5 seconds) collects images of the area around the user (for example the area in front of the user if the mobile device 4 is in the form of a pendant), and detects whether there are any faces in the image. Such technology is well-known in the art (particularly in the art of digital cameras) and need not be described in detail herein. This processing can be performed by the processor 12 in the mobile device 4, although it can alternatively be performed by the processor 28 in the base unit 10. In some implementations, in order to only detect the face of a person actually interacting with the user and not just any face detected in the surrounding environment, the algorithm may require the detected face to have at least a particular size (to make sure that the detected person is close to the user).

Once a face has been detected in the image, the image can be captured (step 107) and sent to the base unit 10 via the transceiver circuitry 6 and antenna 8 for processing by the processor 28. Alternatively, images can be captured regardless of whether a face has been detected, and stored for subsequent use as a retrospective memory aid for the user.

The processor 28 then executes a facial recognition algorithm to try and identify the face in the captured image (step 109). This processing can make use of information stored in the memory 30 relating to people the user knows or has previously had interactions with. This information can include one or more images of the face of the person. The processor 28 can identify the person in the image using any known type of facial recognition algorithm. For example, the processor 28 can use an eigenface-based algorithm to provide the fastest output possible, although those skilled in the art will be aware of other facial recognition algorithms that could be used.

Prior to executing the facial recognition algorithm, pre-processing may be performed in which the input face image is normalized with respect to geometrical properties, such as size and poses and then is further normalized with respect to photometrical properties such as illumination and gray scale, in order to standardize the images to be supplied to the facial recognition algorithm. In addition, pixels in the image around the face that aren't used, such as image background, can be removed, since they change more than the face does.

As mentioned above, a facial recognition algorithm based on eigenfaces can be used. In this algorithm, the first step is to convert color images to greyscale, and then to apply histogram equalization as a method to automatically standardize the brightness and contrast of each facial image. It is useful to apply a low pass filter in order to subtract the noise that is still present in the picture after the initial pre-processing. Eigenfaces uses principal component analysis to reduce the "dimensionality" of images (the number of pixels in an image). The face images are projected into a 'face space' (feature space) which best defines the variation the known test images. The face space is defined by the 'eigenfaces' which are the eigenvectors of the set of faces. These eigenfaces do not necessarily correspond to the distinct features perceived like ears, eyes and noses. The projections of the new image in this feature space are then compared to the available projections of training sets to identify the person. The approach is robust, simple, and easy and fast to implement compared to other algorithms such as 3D imaging. It provides a practical solution to the recognition problem in an automated system that requires a computational time close to real time.

Once the person in the captured image has been identified, the processor 28 retrieves information associated with that person from the memory 30 (step 111). The information can comprise, for example, information on their identity, their relationship to the user and previous topics of conversation with the user. The information can also relate to the purpose of the interaction with the person, which can be derived from an entry in a schedule or calendar for the user. The information about the person and/or interaction can be stored in the form of a video, audio or text data file, for example.

The retrieved information is then sent by the base unit 10 to the mobile device 4 via transceiver circuitry 24 and antenna 26, and the mobile device 4 presents the information to the user (step 113). The information may be presented to the user by either or both of the display 14 and speaker 16, depending on the format of the information (i.e. audio, video, text, etc.) retrieved from the memory 30. It has been found that a visual presentation of information is more effective in triggering the memory of a user with memory impairments or AD, so at least a visual presentation of information is preferred.

Thus, the system 2 provides information about the person with which the user is interacting, or about to interact with, and optionally also about the purpose of the interaction and presents it in a simple form to the user of the system 2, which reduces the effect of poor memory by the user from affecting their interaction with the person.

It will be appreciated that the processing steps described above can be performed in alternative components of the system 2 to those indicated. For example, the facial recognition algorithm could be performed by the processor 12 in the mobile device 4, and only a request for information on the identified person could be transmitted to the base unit 6. Alternatively, all of the images collected by the camera 20 could be transmitted to the base unit 10 in order to detect faces in the images.

In addition to performing facial recognition processing on images of the person the user is interacting with, it is also possible to use voice recognition processing on audio of the person captured using the microphone 18 in the mobile device 4. The output of both types of processing (which can include a provisional identification and a likelihood/confidence value that the recognition is accurate) can be combined and a final identification decision made. The use of both types of processing increases the reliability of the identification of the person.

In an alternative, less-preferred, implementation, it is possible to use voice recognition processing to identify the person the user is interacting with in place of the facial recognition processing described above. However, unlike with the facial recognition implementation, this implementation requires the person to start speaking to the user before any identification can be performed, thus slightly delaying the provision of information about the person to the user.

Returning to step 103, as an optional step alongside the facial recognition process, if the person is not recognized by the user, feedback can be provided by the mobile device 4 to the person (step 115). In this way, the person can be made aware that the user does not recognize them, and they can adapt their behavior during the interaction accordingly. The feedback to the person could comprise a visual (for example text or light-based) and/or audio message from the mobile device 4. A suitable visual cue could be a red light which indicates that the user does not recognize the person or a text-based message that suggests how the person should behave to help the user since the user is not fully responsive.

After step 113 and/or 115, the method moves to step 117 in which the system 2 analyses the interaction to determine the context. If, at step 103, it is determined that the user does recognize the person, the method also passes to step 117. By determining the context of the interaction in step 117, the system 2 will be able to provide relevant support to the user during the interaction, if this is required.

In step 117, if the interaction is one scheduled in an electronic calendar for the user, the system 2 can examine the information stored in the calendar to determine the context of the interaction. For example, the calendar may indicate that the interaction is an appointment with a healthcare professional for discussing their current medication regime, and the system 2 can use this calendar information to determine the context of the interaction. In addition or alternatively, the speech of the user and/or person recorded by the microphone 18 in the system 2 can be converted to text from using a speech processing engine and a natural language processing engine can operate on the text to determine the context of the interaction.

After step 117, the method moves to step 118 in which the system 2 monitors the emotional state and/or stress level of the user during the interaction. The emotional state and/or stress level of the user can be monitored as described above with reference to step 101.

In step 119, it is determined whether the user is stressed. This determination can be made by comparing the physiological characteristic measurements to one or more threshold values, or by mapping the measurements to predetermined emotional states, as shown in FIG. 3.

If it is determined that the user is not stressed at this point in the interaction, the method returns to step 118 and continues monitoring the emotional state of the user during the next part of the interaction.

If it is determined that the user is stressed at this point in the interaction, the method moves to step 121 in which support is provided to the user. The particular support provided to the user can be adapted according to the particular emotional state or stress level of the user. The support can comprise visual and/or audio cues relating to the identity of the person that they are interacting with and the purpose of the interaction determined from the context information derived in step 117.

Furthermore, alongside the support provided for the user, the system 2 may provide feedback on the emotional state of the user to the person they are interacting with (step 123). For example, where the feedback is a visual cue displayed by the mobile device 4, a red display can be used to indicate that the user is stressed. This is similar to step 115 described above, and allows the person to adapt their behavior during the interaction accordingly. After steps 121 and 123, the method returns to step 118 in which the system 2 continues to monitor the emotional state of the user.

Steps 118, 119, 121 and 123 can be implemented by recording the conversation between the user and the person using the microphone 18 in the mobile device 4, dividing it into portions of predetermined length (e.g. 5 seconds) and analyzing the portions to determine if the emotional state of the user is degrading over time (i.e. the user is becoming stressed). The analysis of the conversation can comprise extracting parameters including energy, unvoiced-voiced ratio, pitch range and median pitch, and calculating how they are shifting during time and if they cross an heuristic threshold, which can be based on user data collected during a trial period. For example, if energy, unvoiced-voiced ratio and pitch range are increasing too much there is a high probability that the user is becoming stressed and assistance should be provided to the user by the system 2. In addition, the analysis can detect pauses in the conversation, since a long pause can be indicative of an interruption in the interaction due to the inability of the user to process a question or to remember an event or action.

Thus, a method is provided that assists the user (who has AD or other memory impairment) to recognize the person they are communicating with, reducing the initial confusion for the user and helping to prevent the user's lack of memory translating into stress during an interaction. The method also provides for the monitoring of the user during the interaction in order to determine if further support is required. In addition, the method can provide feedback to the person that the user is interacting with which allows the person to adapt the way in which they are interacting with the user.

As a modification to the above method, the feedback can also be provided to the person that the user is interacting with when the user has recognized them and that the user is not determined to be stressed (i.e. after steps 103 and 119). Where the feedback provided to the user in steps 115 and 123 is provided by the display of a particular color, different colors can be used to indicate different emotional states of the user. For example, if a red display indicates that the user has not recognized the person or is stressed, a green display can be used to indicate that the user has recognized the person or is not stressed.

Another modification to the above method can be to determine whether the user recognizes the person following the presentation of information to the user in step 113. In this case, the method could return to step 101 after the presentation of information in step 113.

Yet another modification to the above method can be to determine whether the user remembers or understands the purpose (context) of the interaction with the person (e.g. to discuss their current medical state, general assistance required, etc.) after the person has been recognized in step 103 or the context of the interaction determined automatically by the system 2 in step 117. In one embodiment, this determination can be made in a similar way to the determination of whether the user recognizes the person they are interacting with in step 101 (e.g. by asking the user directly, monitoring physiological characteristics and/or analyzing the speech at the start of the interaction). If it is determined that the user does not remember or understand the purpose of the interaction with the person, the system 2 can provide suitable information to the user, for example as in step 121, and/or to the person, for example as in step 123. In a similar way, the system 2 can determine whether the user is following and understanding the conversation as the interaction progresses, and provide relevant support as required. This modification is discussed in more detail below with reference to FIG. 5.

A further modification to the above method can be to monitor the emotional state of the person that the user is interacting with (for example by analyzing the speech of the person as recorded by the microphone 18 in the mobile device 4) and using the result of this monitoring to adapt the information provided to the user and/or the feedback provided to the person.

If the user is found to be unresponsive to the person (for example because they do not recognize them or the reason for the interaction), the system 2 can notify or alert the care provider of the situation.

Furthermore, it is possible for the system 2 to process the output of the physiological sensors 24 to determine whether the user's vital signs (e.g. heart rate, heart rate variability, blood pressure, etc.) are within normal ranges, and if not, the care provider can be informed or alerted.

In a further embodiment of the invention, in order to refresh the short term memory of the user about a previous interaction, or an interaction that has just been completed, the system 2 provides information to the user regarding that interaction. The information can also advantageously be used by a healthcare provider or care worker to help train and improve the memory of the user, thereby delaying the progression of AD.

Figure 4:
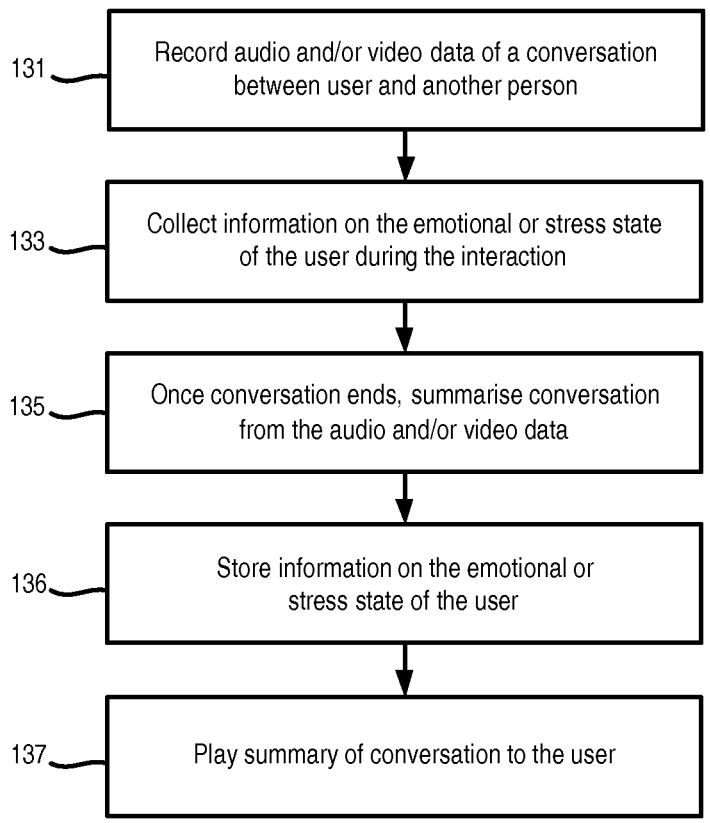
FIG. 4 is a flow chart illustrating a method according to a second embodiment.

A flow chart of the method according to this embodiment of the invention is shown in FIG. 4. In step 131, the mobile device 4 collects audio and/or video data during the interaction between the user and the person.

The mobile device 4 sends this data to the base unit 10 for processing as it is collected, or alternatively after the interaction has ended (which can be determined by, for example, detecting that the person is no longer facing or near the user, and/or that the microphone 18 does not detect speech by the user for more than a predetermined period of time).

Optionally, in step 133, the system 2 can also collect information on the emotional state of the user during the interaction (for example using the physiological sensor(s) 24 or analysis of the user's speech, as described above).

The processor 28 in the base unit 10 receives the audio and/or video data from the mobile device 4 and optionally the information on the emotional state of the user during the interaction, and executes an algorithm with the data to generate a summary of the interaction between the user and the person (step 135). This algorithm can include a speech recognition algorithm for converting the speech in the data into text, a content recognition algorithm (e.g. a natural language processing algorithm) for determining the meaning of the spoken words and an algorithm for extracting and summarizing the important points of the interaction. The summary will include information about the interaction, such as the person involved, the topics covered, any instructions given (for example by a care worker), the time and date of the interaction, etc. The information on the emotional state of the user can be used to adapt the information to be included in the summary. For example, where the processor 28 identifies that the user had difficulty remembering a particular event or response (as indicated by a comparison of the emotional state information to the audio and/or video data), information on the event or required response can be included in the summary.

In step 136, the information on the emotional state of the user, and optionally other information relating to an interaction (for example the persons involved, the topics of conversation, etc.), may be stored in the memory 30 of the base unit 10 for subsequent review and use by a care worker.

The summary (which may be in text, audio and/or video format) is then transmitted to the mobile device 4 which presents it to the user using the visual display 14 and/or speaker 16 as appropriate (step 137). The mobile device 4 may present the summary to the user straight after the completion of the interaction, or a predetermined time after the completion of the interaction, or at a predetermined time of day. The mobile device 4 may also include some means for catching the attention of the user at the appropriate time before presenting the summary to the user. This means may include vibrating the mobile device 4 (and varying the frequency and/or intensity of the vibration), generating an audio indication and/or a visual indication.

This method allows the user to review and recall the interaction after the interaction has finished, which helps to improve their memory. This also allows the user's interactions to be reviewed by a care provider in order to assess the user's progress and particular things or people that the user has difficulty remembering. In addition, information derived from summaries of previous interactions can be used to influence the decision on whether to provide support to the user during subsequent interactions.

As the system 2 is directed towards assisting people with memory impairments, the generated summary should be simple to understand and follow. The speech in the summary should consist of relatively short sentences which are grammatically formed to make them easy to follow (for example, people with AD are generally not able to process pronouns, so the sentence should be structured to avoid or minimize their use). In addition the speech rate should be relatively slow, and the speech itself should be loud and intelligible. In addition to the speech/audio, the summary can also include other multimedia content (for example pictures, video) that are recorded during the conversation. The care provider can select the speech characteristics (rate, loudness, type, pitch, spectral coloring. etc.) and multimedia content (type, duration, size, etc.) that are to be used in generating the summary, since the care provider knows the needs of the user.

In some embodiments, the summaries provided to the user and to the care provider or doctor can be different. For example, the summary for the care provider or doctor aim to capture as much as data about the interaction as possible, so that the care provider is informed about the user (for example about the user's capability to communicate and interact, about their health and emotions, about their daily schedule and daily life). In addition to the interaction (speech, images or video) these summaries can also include data from the physiological sensors and information showing the user's emotional state.

In some embodiments, the care worker can adjust the operation of the mobile device 4 (possibly via the base unit 10 or other remote station). The care worker may be able to adjust the visualization options (i.e. the type and/or content of the visual output) provided by the mobile device 4, the audio level setting, the alerts for the user and person that the user is interacting with that can be activated by the mobile device 4, the user's schedule or calendar (for example the care worker can add new appointments for the user, additional information about existing appointments, the people involved, the purpose or aim of the appointment, etc.) and activate or deactivate certain functions within the system 2 (such as the measurement of the user's and/or person's emotional response, generation of the summary of the interaction, etc.).

Figure 5:
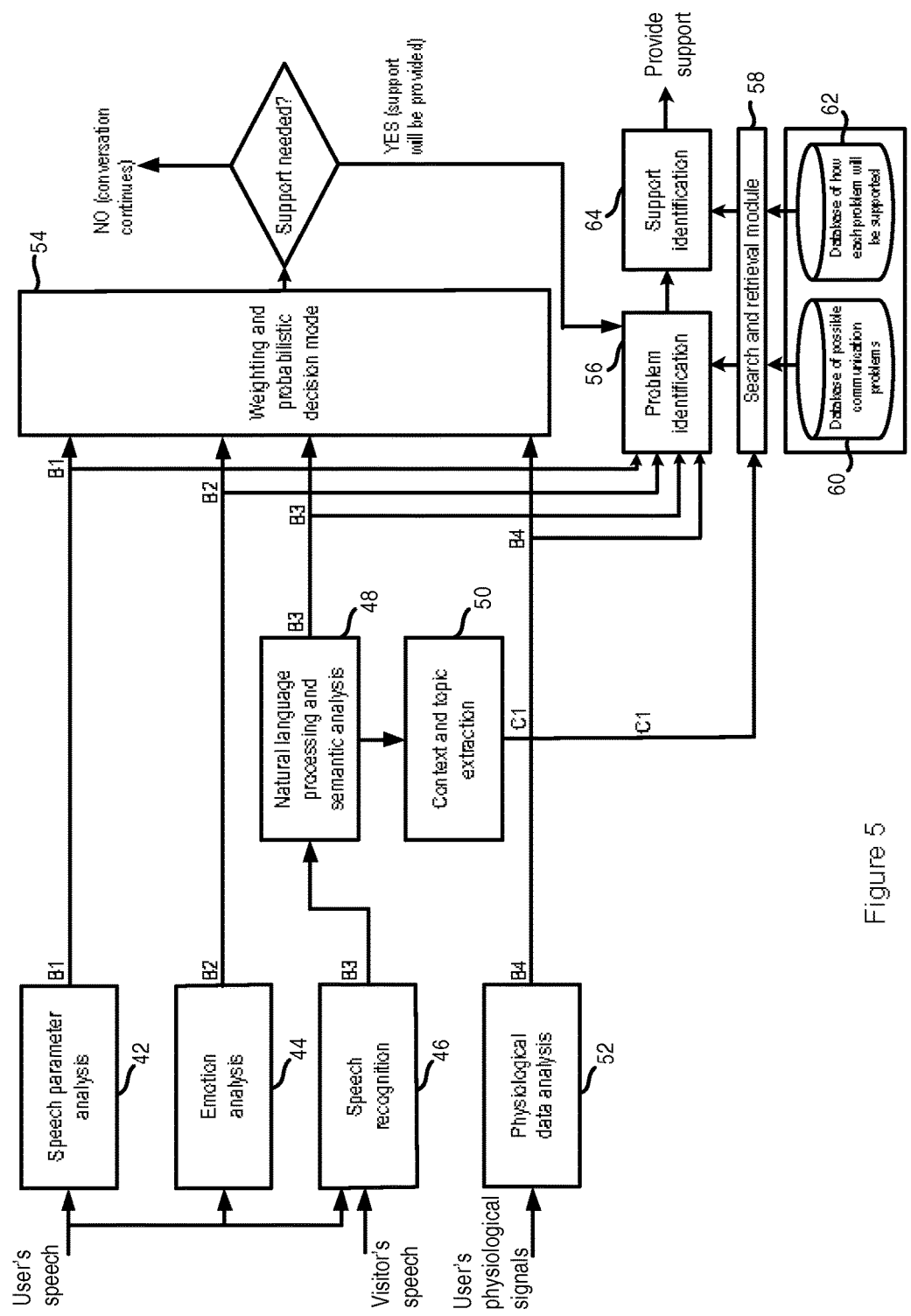
FIG. 5 illustrates modules for monitoring an interaction in an embodiment of the invention.

FIG. 5 illustrates a number of modules used to monitor and provide support to a user during an interaction according to an embodiment of the invention. The operation of these modules generally corresponds to steps 117-123 in FIG. 2, and they seek to monitor the interaction by observing if the user is able to understand and respond to the person they are interacting with. The monitoring is done by simultaneously analyzing different aspects of users speech and physiological signals, as described below. The information extracted from each of the modules is combined to determine if it is necessary to provide support to the user or not.

The user's speech, as recorded by microphone 18 is input to a speech parameter analysis module 42 and an emotion analysis module 44 and a speech recognition module 46. The speech of the person the user is interacting with is also input to the speech recognition module 46.

The speech parameter module 42 examines the speech of the user to determine whether long silences, hesitations, changes in breathing, changes in speech quality, and conversation breaks occur during the interaction. These characteristics may indicate that user is not able to follow the conversation. The output of this module 42 is denoted B1 in FIG. 5.

The emotion analysis module 44 examines the speech of the user to determine their emotion. If the speech parameters (such as pitch, rate, energy, spectral characteristics, silences, sentence duration, breathing and/or loudness) indicate diversion from the user's normal (usual) state, this may indicate that support is useful. This module 44 can be used to build a probabilistic model of the user's normal state, and then periodically check if the speech parameters during subsequent interactions fit the model or not. The output of this module 44 is denoted B2 in FIG. 5.

The speech recognition module 46 processes the user's and person's speech, and converts the recognized speech to text. This text is subsequently analyzed by a natural language processing engine 48 to determine if the conversation (dialogue) during the interaction is meaningful and healthy and if there are words or phrases that may indicate that support is required. The output of this module 48 is denoted B3 in FIG. 5.

In addition, the text is processed by a context and topic extraction module 50 to identify meaningful words in order to reconstruct the topic and the context of the conversation. The information is then used to tailor the support provided to the user to be context aware and thus more effective. The output of this module 50 is denoted C1 in FIG. 5.

In addition to the analysis of speech, a physiological data analysis module 52 is provided that receives signals from the physiological characteristic sensor(s) 24 in or associated with the mobile device 4 and determines the user's physiological response to and during the interaction. The responses are also used to monitor the interaction and to determine if support is needed. For example, using wearable physiological characteristic sensors 24 (that transfer information to the mobile device 4), the user's heart rate, heart rate variability, skin conductance, skin temperature and breathing patterns can be measured. The relaxation or stress state of the user can be determined from the physiological sensor data. The output of this module 50 is denoted B4 in FIG. 5.

The outputs of modules 42, 44, 48 and 52 are provided to a weighting and probabilistic decision module 54 and a problem identification module 56. The output from the context and topic extraction module 50 is provided to a search and retrieval module 58. The search and retrieval module 58 interfaces with two databases 60, 62 that store a information on possible communication problems the user might have (database 60) and information on how each problem is to be supported (database 62).

The weighting and probabilistic decision module 54 processes the information from the modules 42, 44, 48 and 52 and determines if support is required for the user during the interaction. If it is determined that no support is required, the system 2 allows the interaction to continue without intervening to provide support to the user. If, however, it is determined that support is required, the problem identification module 56 is activated and obtains information on the problem the user is having from database 60 via the search and retrieval module 58.

After the problem has been identified, a support identification module 64 is used to determine the specific support that is to be provided to the user. The support identification module 64 uses the identified problem, output C1 from the context and topic extraction module 50 and the information stored in database 62 to determine the required support. The database 62 may store the information on the support to be provided in respect of the possible problems the user may have during an interaction in the form of a look-up table. Once the required support is identified, the support is provided to the user.

For example, if by monitoring the interaction, it is determined that user is not able to recognize the person, a video showing the user's previous encounters with the person is played; if the purpose of the visit is not recognized by the user, this is again provided visually; if it is detected that the user is angry, the person can be informed about this; if it is detected that the user is tired, the person can be informed about this and they can conclude the conversation accordingly. In short, for each outcome or problem that may come from the monitoring stage, there is a support path that will be followed.

In a preferred embodiment, the functionality of each of the modules shown in FIG. 5 is provided by the processor 28 in the base unit 10.

Figure 6:
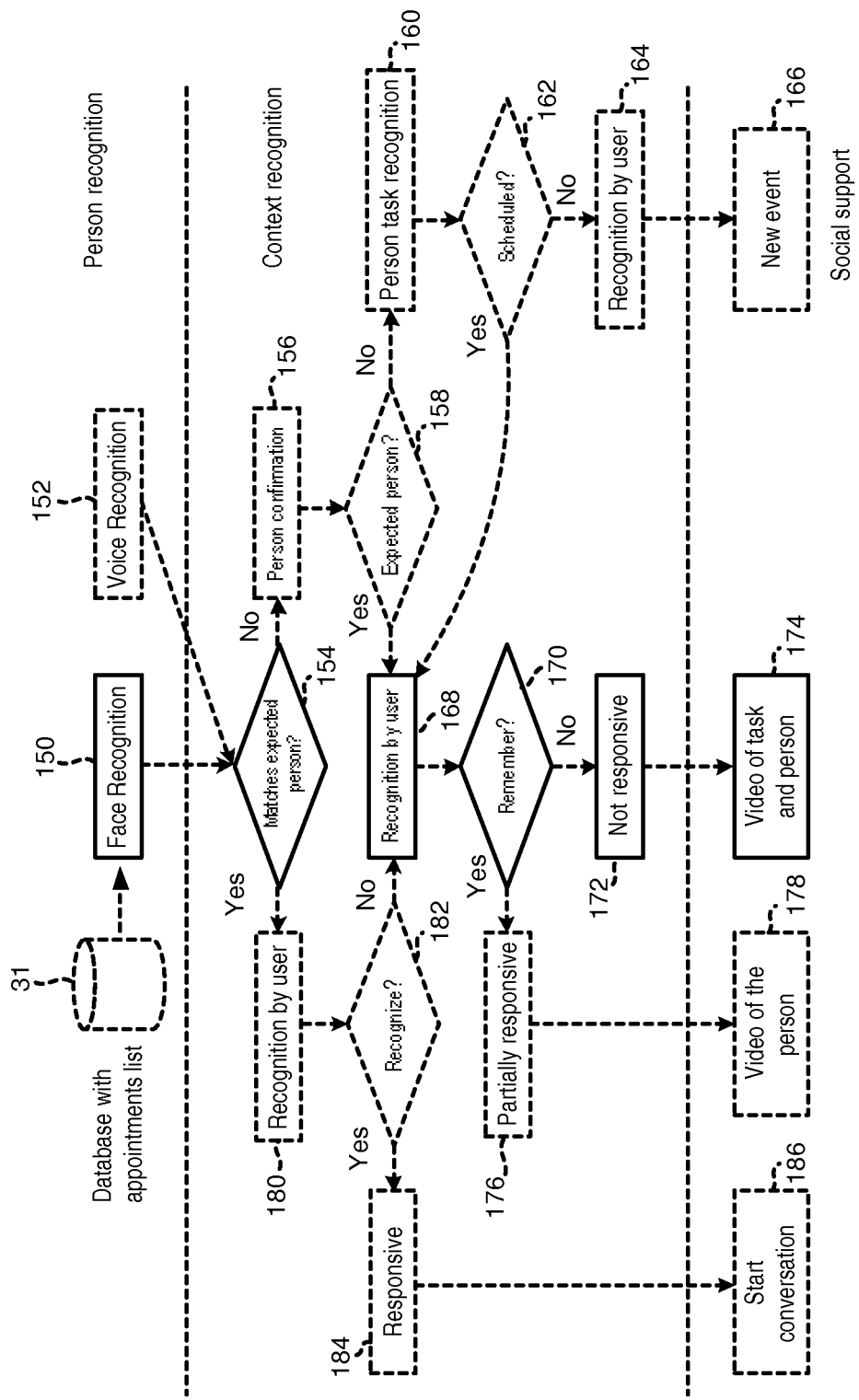
FIG. 6 is a flow diagram showing the operation of a system according to an embodiment of the invention.

A specific embodiment of the interaction monitoring and support according to the invention is shown by the flow diagram in FIG. 6. This flow diagram aims to illustrate a possible model of a social interaction, in which two people approach, they greet each other, the user remembers the reason why they decided to meet, and they start interacting. All those steps are trivial for healthy people, but a person with memory and cognitive impairment would have severe problems in performing them, accumulating stress and isolating himself. In the event that the user remembers the task to be performed, but does not recognize the person in front of them, the mobile device 4 alerts the person of what should be done to help. Then the device 4 shows the user information in the form of a video about the person or, if available, about the user and the person together in order to evoke his memory. In the case that the user does not remember either the person or the reason of the visit, the mobile device 4 switches to a mode of total support. In this mode, the person is notified about the situation, and information is presented to the user about the person and the task to be performed.

Thus, during a person recognition stage, facial and voice recognition (denoted 150 and 152 respectively) are performed for a person the user is about to interact with or has just started to interact with. The person recognition stage also makes use of an appointments list for the user that is stored in a database (for example database 31 in the base unit 10), with the appointments list indicating the person expected to interact with the user.

If the person identified by the facial and voice recognition does not match (154) the expected person (according to the information in the appointments list), the mobile device 4 communicates with the person (156) to understand if the result of the recognition was right or wrong. In 156, the person can be asked to confirm their name, which will be recorded by microphone 18 and the speech analyzed to extract the spoken name. If the result of the recognition was wrong and the person is the one expected, the system 2 moves to a task/interaction recognition stage (168 onwards).

If the result of the recognition was correct and the person is not one scheduled to interact with the user at that time, the system 2 determines (160) if the reason for the visit is the same as the expected one (for example a different nurse to the one scheduled could be sent to deliver medications) or if they are there for a different reason. In 160, the mobile device 4 can ask the person the purpose of their visit, and the speech recognition algorithm can be used to understand the reply. If the reason for the visit is different to the one scheduled, the mobile device 4 notifies the user about the new interaction (164) and creates a new event in the appointments list (166).

If the reason for the visit is the same as the one scheduled (but with a different, known person) or if the person is the one expected for the interaction (from 158), the mobile device 4 notifies the user of the scheduled interaction (168). If the user does not remember and/or understand the reason for the interaction (170) (and also the person, since they are not the one scheduled to interact with the user), the user is considered to be non-responsive (172) and the mobile device 4 provides information on the purpose of the interaction and the identity of the person to the user (174). A care provider for the user can also be alerted that the patient is non-responsive.

If the user does remember the purpose of the visit/interaction (170), the user is considered to be partially responsive (176) and information on the identity of the person is provided to the user by the mobile device 4 (178).

If at 154 the result of the facial and voice recognition matches the expected person, it is determined whether the user recognizes them (180). This can be done by playing an audio message to the user asking them if they recognize the person. The speech processing algorithm can be used to interpret the reply spoken by the user. If the user does recognize the person, the user can be assumed to be responsive (184) and no support is required at this time. The system 2 can then allow the conversation to start (186) without having to provide any support to the user or feedback to the person.

The device 4 then enters a conversation support mode, where it records the conversation and provides feedback if the user's memory impairments are blocking the flow of conversation.

If the user does not recognize the person (182), it is determined whether the user recognizes the reason for the visit, even though they do not recognize the person (168). The system 2 then proceeds as described above (170-178).

There is therefore provided a method and system for assisting a person having memory impairments in social interactions.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method, comprising:
    measuring, with a sensor of a mobile device, a physiological characteristic of a user interacting with a person;
    transmitting the physiological characteristic to a base station, which maps the physiological characteristic to a stress level;
    receiving a signal from a transceiver of the base station indicating the stress level;
    determining, with a processor, the user does not recognize the person based on the stress level;
    identifying, with the processor, the person;
    providing, with the processor, information about the person and stored in memory to the user so that the user recognizes the person.

2. The method as claimed in claim 1, wherein determining the user does not recognize the person includes: analyzing the interaction over time to detect if the stress level increases over time.

3. The method as claimed in claim 1, wherein determining the user does not recognize the person includes: detecting a pause in the interaction due to an inability of the user to process a question or to remember an event or action.

4. The method as claimed in claim 1, wherein the signal includes a probabilistic value indicating a reliability level of the stress level.

5. The method as claimed in claim 1, wherein the physiological characteristic is from a group consisting of a heart rate, a skin conductivity, a breathing rate or a perspiration.

6. The method as claimed in claim 1, wherein mapping the physiological includes characterizing the physiological characteristic as an overall happiness encoded as positive, neutral or negative, and an intensity encoded as excited, neutral or calm.

7. The method as claimed in claim 1, further comprising:
    determining a context of the interaction based on the interaction.

8. The method as claimed in claim 7, wherein the interaction is an event scheduled in an electronic calendar, and further comprising:
    determining the context of the interaction based on an entry in the electronic calendar.

9. The method as claimed in claim 8, wherein the entry is for a medical examination, and further comprising:
    determining the context of the interaction based on the medical examination.

10. The method as claimed in claim 1, wherein identifying the person includes identifying the person with facial recognition technology.

11. The method as claimed in claim 1, wherein identifying the person includes identifying the person with voice recognition technology.

12. The method as claimed in claim 1, wherein providing information includes visually displaying the information via a display monitor.

13. The method as claimed in claim 1, wherein providing information includes audibly presenting the information via a speaker.

* * * * *